US010194935B2

(12) United States Patent
Grez

(10) Patent No.: US 10,194,935 B2
(45) Date of Patent: Feb. 5, 2019

(54) SHEAR-INDUCED DERMAL INFUSION

(71) Applicant: L'Oreal, Paris (FR)

(72) Inventor: Joseph W. Grez, North Bend, WA (US)

(73) Assignee: L'Oreal, Paris (FR)

(*) Notice: Subject to any disclaimer, the term of this patent is extended or adjusted under 35 U.S.C. 154(b) by 871 days.

(21) Appl. No.: 14/145,179

(22) Filed: Dec. 31, 2013

(65) Prior Publication Data
US 2015/0182246 A1 Jul. 2, 2015

(51) Int. Cl.
A61B 17/3205 (2006.01)
A61M 37/00 (2006.01)
(Continued)

(52) U.S. Cl.
CPC .......... A61B 17/3205 (2013.01); A45D 44/00 (2013.01); A61H 7/005 (2013.01);
(Continued)

(58) Field of Classification Search
CPC ........ A61B 2017/00761; A61B 17/322; A61B 2017/320004; A61B 2017/320008; A61B 2017/320012; A61B 17/54; A61B 2017/00752; A61B 2017/00747; A61B 2017/320076; A61B 2018/0047; A45D 26/0023; A45D 2200/1054; A45D 2200/1018; A45D 26/0004; A45D 26/0028; A46B 2200/3093; A46B 5/0012;
(Continued)

(56) References Cited

U.S. PATENT DOCUMENTS 4,777,599 A 10/1988 Dorogi
5,084,046 A * 1/1992 Isack .................. A45D 26/0004
606/133
(Continued)

FOREIGN PATENT DOCUMENTS

CN 101128136 A 2/2008
WO 2004/064567 A2 8/2004
(Continued)

OTHER PUBLICATIONS

International Preliminary Report on Patentability dated Jul. 14, 2015, issued in corresponding International Application No. PCT/US2014/063216, filed Oct. 30, 2014, 7 pages.
(Continued)

Primary Examiner — Michael Tsai
Assistant Examiner — Christopher Miller
(74) Attorney, Agent, or Firm — Christensen O'Connor Johnson Kindness PLLC

(57) ABSTRACT

Treatment protocols for preparing a subject's skin to receive skin formulations having one or more active materials are provided. The devices and/or methods for carrying out the treatment protocols aim to increase the skin's ability for skin formulations to penetrate or infuse into the SC layers thereof. The treatment protocol includes the application of shearing forces in order to part, tear, or form fissures only in the Stratum Corneum (SC) of the subject's skin without inducing trauma in viable skin layers below the SC. After application of shearing forces to the skin, a skin formulation can be applied to the sheared areas of skin.

17 Claims, 3 Drawing Sheets

(51) Int. Cl.
  *A61H 7/00* (2006.01)
  *A61M 35/00* (2006.01)
  *A45D 44/00* (2006.01)
  *A61H 23/02* (2006.01)
  *A61B 17/32* (2006.01)
  *A61B 17/00* (2006.01)

(52) U.S. Cl.
  CPC ....... *A61H 23/0254* (2013.01); *A61M 35/003* (2013.01); *A61M 37/00* (2013.01); *A45D 2200/20* (2013.01); *A61B 2017/00747* (2013.01); *A61B 2017/00761* (2013.01); *A61B 2017/320008* (2013.01); *A61H 2201/149* (2013.01); *A61H 2201/1678* (2013.01); *A61M 2037/0007* (2013.01)

(58) Field of Classification Search
  CPC .......... A61M 2037/0007; A61M 37/00; A61H 2201/1678
  See application file for complete search history.

(56) References Cited

U.S. PATENT DOCUMENTS

| | | | | |
|---|---|---|---|---|
| 5,416,942 | A * | 5/1995 | Baldacci | A61C 17/349 15/22.1 |
| 5,647,841 | A * | 7/1997 | Groenewold | A46B 13/04 15/29 |
| 5,891,063 | A * | 4/1999 | Vigil | A46B 13/02 15/207.2 |
| 5,964,729 | A * | 10/1999 | Choi | A61B 17/205 604/47 |
| 6,032,313 | A * | 3/2000 | Tsang | A46B 13/02 15/21.1 |
| 6,139,553 | A | 10/2000 | Dotan | |
| 7,157,816 | B2 * | 1/2007 | Pilcher | H02K 33/16 310/36 |
| 7,363,673 | B2 * | 4/2008 | Schonewille | A47L 13/26 15/29 |
| 7,678,120 | B2 * | 3/2010 | Shadduck | A61B 17/54 604/289 |
| 7,786,626 | B2 * | 8/2010 | Reishus | H02K 33/16 15/22.1 |
| 8,048,089 | B2 * | 11/2011 | Ignon | A61B 17/545 606/131 |
| 2002/0049398 | A1 * | 4/2002 | Wevers | A46B 13/00 601/84 |
| 2002/0111600 | A1 * | 8/2002 | Cormier | A61B 17/205 604/506 |
| 2003/0093040 | A1 * | 5/2003 | Mikszta | A61B 17/54 604/289 |
| 2003/0125754 | A1 * | 7/2003 | Davis | A45D 26/0004 606/133 |
| 2004/0015139 | A1 * | 1/2004 | La Bianco | A61B 17/54 604/289 |
| 2004/0064087 | A1 * | 4/2004 | Lastovich | A61B 17/205 604/46 |
| 2004/0092959 | A1 * | 5/2004 | Bernaz | A61B 17/54 606/131 |
| 2004/0167481 | A1 * | 8/2004 | Carlucci | A45D 26/0004 604/291 |
| 2004/0210214 | A1 * | 10/2004 | Knowlton | A61B 18/14 606/41 |
| 2004/0236269 | A1 * | 11/2004 | Marchitto | A61M 37/00 604/22 |
| 2004/0254587 | A1 * | 12/2004 | Park | A61B 17/54 606/131 |
| 2005/0038448 | A1 | 2/2005 | Chung | |
| 2005/0143754 | A1 * | 6/2005 | Zelickson | A61B 17/54 606/131 |
| 2005/0277950 | A1 * | 12/2005 | Pilcher | A61B 17/54 606/131 |
| 2005/0278876 | A1 * | 12/2005 | Roth | A46B 13/06 15/28 |
| 2005/0278877 | A1 | 12/2005 | Akridge | |
| 2006/0047234 | A1 * | 3/2006 | Glucksman | A45D 26/0004 601/87 |
| 2006/0130266 | A1 * | 6/2006 | Brown | A61B 17/20 15/329 |
| 2006/0130335 | A1 * | 6/2006 | Suen | A45D 26/0004 30/34.05 |
| 2007/0293795 | A1 * | 12/2007 | Carroll | A61B 17/54 601/138 |
| 2009/0005659 | A1 | 1/2009 | Kollias | |
| 2009/0124985 | A1 * | 5/2009 | Hasenoehrl | A45D 34/04 604/289 |
| 2009/0157094 | A1 * | 6/2009 | Yeshurun | A61B 17/54 606/131 |
| 2009/0177125 | A1 * | 7/2009 | Pilcher | A46B 15/0034 601/18 |
| 2009/0177171 | A1 * | 7/2009 | Ignon | A61B 17/54 604/289 |
| 2009/0198159 | A1 * | 8/2009 | Linzell | A61H 7/003 601/138 |
| 2010/0049177 | A1 * | 2/2010 | Boone, III | A61H 9/0057 606/9 |
| 2010/0242201 | A1 * | 9/2010 | Linzell | A45D 34/04 15/229.11 |
| 2011/0120487 | A1 * | 5/2011 | Rollat-Corvol | A45D 19/16 132/200 |
| 2012/0233798 | A1 * | 9/2012 | Brewer | A46B 9/06 15/160 |
| 2013/0060176 | A1 * | 3/2013 | Nichols | A46B 13/023 601/137 |
| 2013/0204178 | A1 * | 8/2013 | Luzon | A61N 1/044 604/20 |
| 2014/0148823 | A1 * | 5/2014 | Fitzsimons | A61B 17/54 606/131 |
| 2014/0305458 | A1 * | 10/2014 | Brewer | A45D 34/041 132/200 |
| 2014/0330289 | A1 * | 11/2014 | Revivo | A61B 17/54 606/131 |
| 2015/0202114 | A1 * | 7/2015 | Pardoel | A61H 7/005 601/112 |

FOREIGN PATENT DOCUMENTS

WO 2005/065551 A2 7/2005
WO 2005/091748 A2 10/2005

OTHER PUBLICATIONS

International Search Report dated Feb. 25, 2015, issued in corresponding International Application No. PCT/US2014/063216, filed Oct. 30, 2014, 6 pages.
Written Opinion dated Feb. 25, 2015, issued in corresponding International Application No. PCT/US2014/063216, filed Oct. 30, 2014, 6 pages.
De Boer, M., et al., "Guidelines for Etching Silicon MEMS Structures Using Fluorine High-Density Plasmas at Cryogenic Temperature," Journal of Microelectromechanical Systems 11(4):385-401, Aug. 2002.
Falke., M., "Mechanical Behaviour of Human Epidermal and Dermal Layers in Vivo," PhD Dissertation, Technische Universiteit Eindhoven,The Netherlands, 2005, 119 pages.
Geerligs, M., "A Literature Review of the Mechanical Behavior of the Stratum Corneum, the Living Epidermis and the Subcutaneous Fat Tissue," Technical Note PR-TN 2006/00450, Philips Research Europe, Jun. 2006, 39 pages.
O'Mahony, C., "Silicon-Based Microneedles for Painless Percutaneous Penetration," Tyndall National Institute <http://www.tyndall.ie/content/microneedle-technology> [retrieved Sep. 10, 2014], 7 pages.
White, C., and Frangos, J., "The Shear Stress of It All: the Cell Membrane and Mechanochennical Transduction," Philosophical Transactions of the Royal Society B 362(1484):1459-1467, Aug. 2007.

(56) References Cited

OTHER PUBLICATIONS

Notification of the First Office Action dated Jul. 9, 2018, issued in corresponding Chinese Application No. 201480065454.5, filed Oct. 30, 2014, 20 pages.

* cited by examiner

SHEAR-INDUCED DERMAL INFUSION

BACKGROUND

Current skin care treatment protocols typically involve the absorption or penetration of a skin formation into the epidermis for effective results. However, the Stratum Corneum (SC), the topmost and thinnest layer of the epidermis, is said to be 1000 times more resistive as a natural barrier than the underlying viable epidermis. As a result, skin formulations applied to the skin often do not reach the lower layers of the epidermis as intended.

Current techniques for aiding infusion of a skin formulation having active materials to the epidermis include micro needles, electrophoresis, ultrasound, dermal/micro-dermal abrasion, and chemical peels. These methods are either not effective on all types of fluids or are associated with pain, bleeding, and infection.

However, currently there are no devices and/or methods that improve infusion of skin formula penetration into the SC without affecting the underlying viable tissues, and which preferably work in a painless, infection-free manner.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with aspects of the present disclosure, a skin treatment apparatus is provided. The apparatus includes a shear inducing head having a first friction surface adjacent a first edge, and a second friction surface adjacent a second edge, which is spaced a constant distance from the first edge in order to form a gap having a width of between about 0.003 mm and 0.200 mm. The apparatus also includes a drive motor assembly configured to impart an oscillating motion to the shear inducing head such that the first friction surface moves with respect to the second friction surface in an oscillating manner.

In accordance with another aspect of the present disclosure, a method is provided for applying shear force to a subject's skin. The method includes oscillating a shear inducing head having a first member oscillating at a selected amplitude and frequency with respect to a second member. The first and second members are spaced a constant distance apart and define first and second gripping surfaces, respectively. The method also includes contacting the shear inducing head to a region of the subject's skin.

In accordance with another aspect of the present disclosure, a method is provided for infusing a skin formulation into at least a portion of the user's epidermis, including the SC. The method includes applying shear force to a region of a subject's skin, thereby defining sheared areas of skin, and applying a skin formulation to the sheared areas of skin.

DESCRIPTION OF THE DRAWINGS

The foregoing aspects and many of the attendant advantages of this disclosed subject matter will become more readily appreciated as the same become better understood by reference to the following detailed description, when taken in conjunction with the accompanying drawings, wherein.

DETAILED DESCRIPTION

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The following discussion provides examples of treatment protocols and associated devices that relate to skin care. In some treatment protocols described herein, devices and/or methods are provided that prepare a subject's skin to receive skin formulations having one or more active materials. In particular, the following discussion provides examples of devices and/or methods for treating a subject's skin in order to increase the skin's ability for skin formulations to penetrate or infuse into the SC layers thereof. As will be described in more detail below, the treatment protocol includes the application of shearing forces in order to part, tear, or form fissures only in the Stratum Corneum (SC) of the subject's skin without inducing trauma in viable skin layers below the SC.

Embodiments of the present disclosure include devices and methods that employ a skin contacting head with at least one surface or part that is movable with respect to another adjacent surface or part. In some embodiments, either one or the other surface or part can be moved with respect to the other. In other embodiments, both parts are movable opposite one another. The moving part or parts of the device, when applied to either wet or dry skin, aim to produce surface shear regions that create tears or fissures in only the SC.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1:
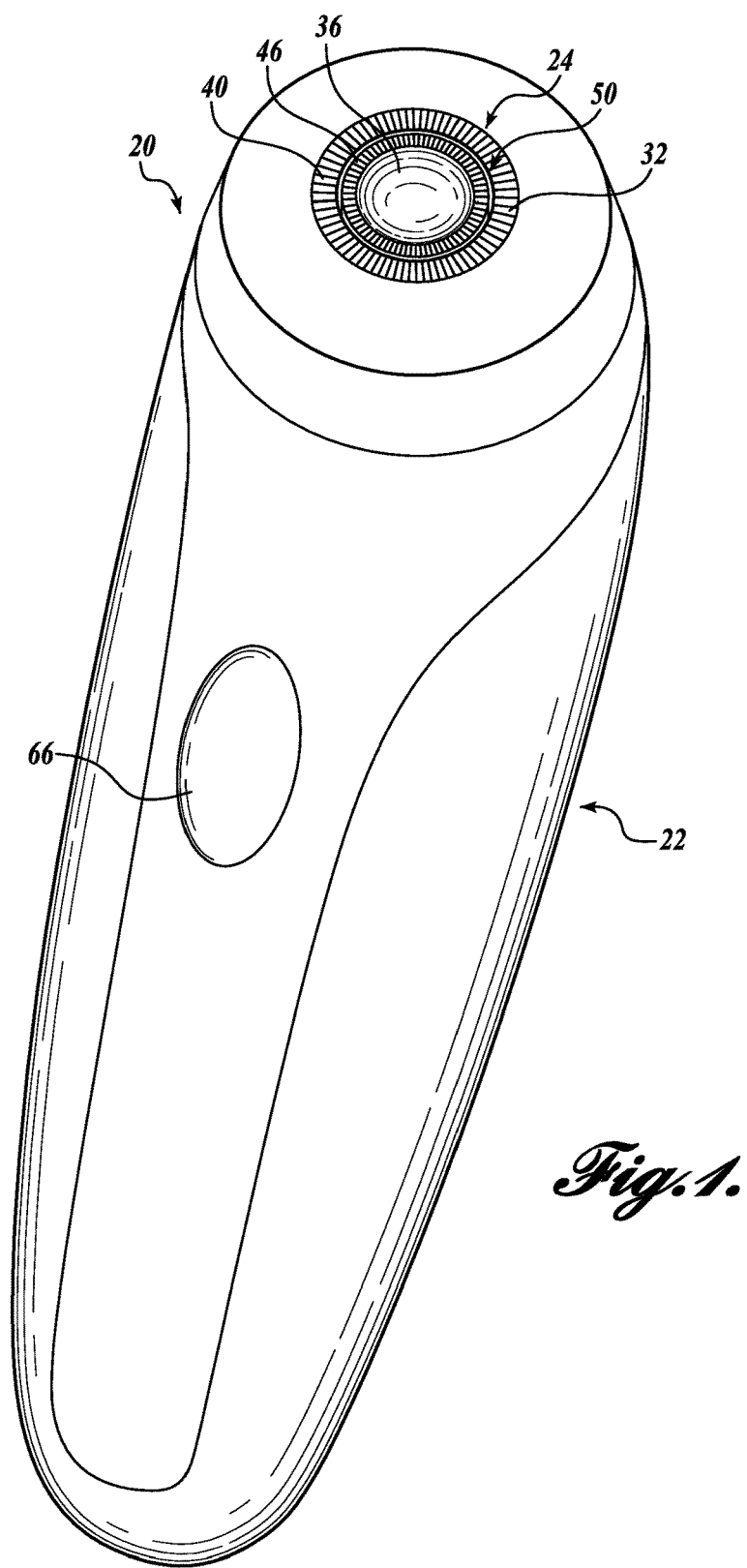
FIG. 1 is a perspective view of one example of a skin treatment apparatus formed in accordance with aspects of the present disclosure.

Turning now to FIG. 1, there is shown one example of a skin care apparatus, generally designated 20, formed in accordance with aspects of the present disclosure. The apparatus 20 includes a shear inducing head 24 operatively mounted at the end of a powered appliance 22. The shear inducing head 24 in some embodiments includes a fixed or stationary outer ring 32 that surrounds a rotatable central disc 36. The outer diameter of the outer ring 32 is up to about 20-25 mm or greater in some embodiments, and about 10 mm in certain embodiments. The outer diameter of the circular disc 36 in some embodiments is between about one (1) mm and 20 mm, and between about four (4) mm and eight (8) mm or greater in certain embodiments. In some embodiments, the outer ring 32 and the central disc 36 are made from steel, although other rigid, biocompatible metals or plastics can be used.

Figure 2:
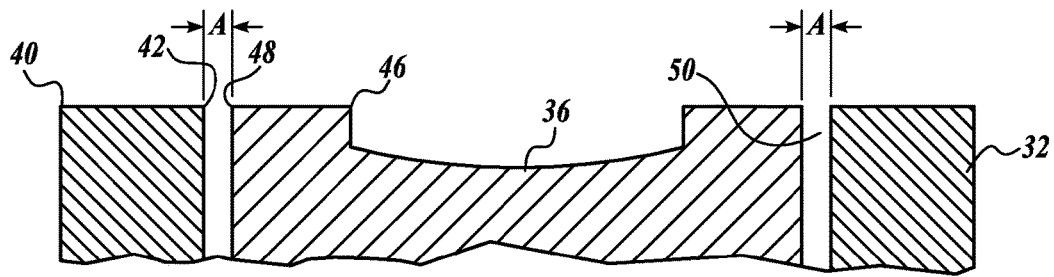
FIG. 2 is an enlarged partial, cross-sectional view of one example of the shear inducing head of the skin treatment apparatus of FIG. 1.

As shown in the enlarged, partial cross-sectional view of FIG. 2, the inner perimeter region of the outer ring 32 includes a first gripping surface 40 disposed adjacent an inner edge 42. The outer perimeter region of the central disc 36 includes a second gripping surface 46 disposed adjacent an outer edge 48 and general co-planar with first gripping surface 40. The first and/or second gripping surfaces 40, 46 in some embodiments have a width of between about one (1) and 10 mm, and about three (3) mm in certain embodiments. The gripping surfaces 40, 46 need not have the same width. The outer ring 32 surrounds the central disc 36 such that a constant circular gap 50 is formed between opposing edges 42 and 48. In several embodiments, the thickness of the gap, designated A in FIG. 2, is on the order of the SC thickness so as to limit the shear strains to only the SC. In order to account for varying moisture levels of the SC, the gap A in some embodiments is in the range of between about 0.003 millimeters and 0.200 millimeters, and between about 0.010 mm and 0.015 mm in certain embodiments.

Figure 4:
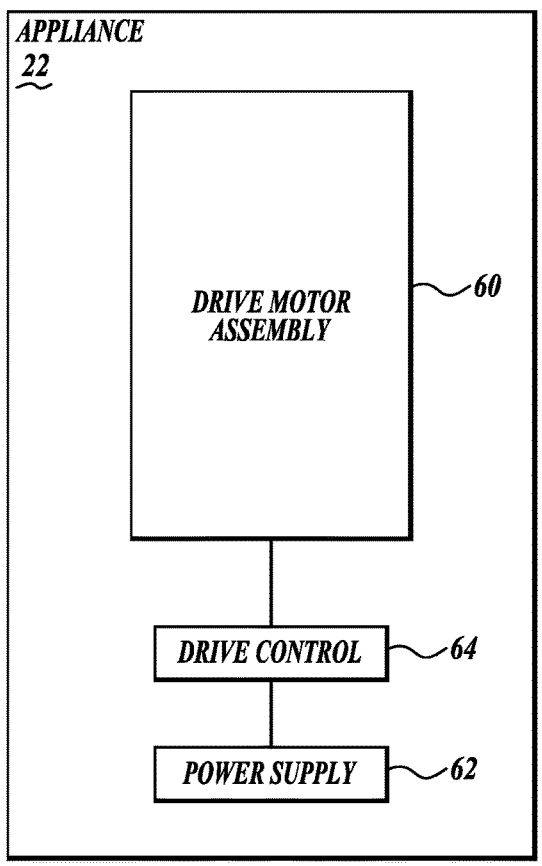
FIG. 4 is a functional block diagram of several components of a powered appliance of FIG. 1.

Referring to FIGS. 1 and 4, the powered appliance 22 includes a drive motor assembly 60 to provide rotational motion to the central disc 36 in an oscillating or back and forth manner. In that regard, the drive motor assembly 60 is connected to a power supply 62 via a drive control 64 that includes an on/off button 66 (see FIG. 1). The on/off button and associated circuitry is configured and arranged to selectively deliver power from the power supply 62 to the drive motor assembly 60. In some embodiments, the power supply 62 includes a power storage source, such as a rechargeable battery. In other embodiments, a power cord coupled to the power supply supplies power via a "mains" power source.

In some embodiments, the drive motor assembly 60 is configured to oscillate the central disc 36, back and forth with respect to the outer ring 32 between an angular range or amplitude α (see FIGS. 3A-3C) of between about 0.1 and about 3.4 degrees, or greater, and at a frequency of between, for example, 10-400 Hz (between 100-150 Hz in certain embodiments). It will be appreciated that the oscillation amplitude imparted to the central disc 36 by the drive motor assembly 60 could be varied, depending in part on its intended application and/or characteristics of the subject's skin, including moisture levels in the SC. The drive motor assembly 60 in some embodiments includes an electric rotary drive motor and an optional rotary to oscillating/reciprocating motion mechanism for imparting the oscillatory motion to the central disc 36. In other embodiments, the drive motor assembly 60 includes an electrical motor that moves an associated armature, to which the central disk is coupled, in an oscillating manner via vibration, etc.

Figures 3A, 3B:
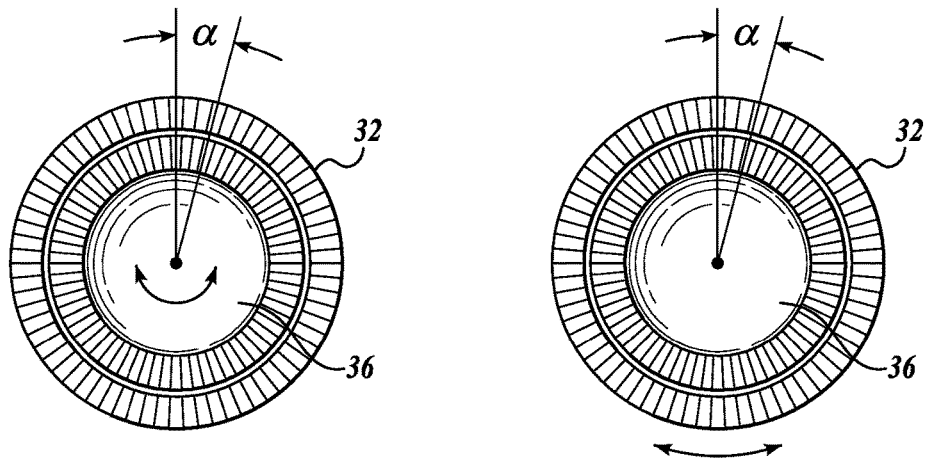
FIGS. 3A-3C are various examples of the relative motion of the outer ring and the central disc.
Figure 3C:
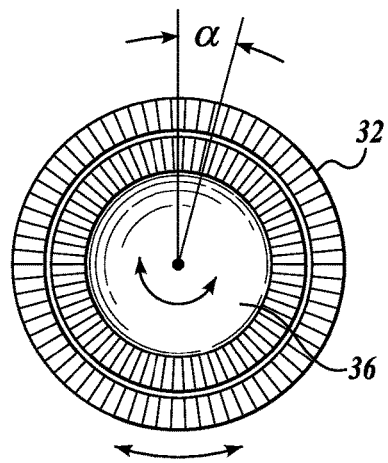

While in the embodiments described above, the outer ring 32 is fixed in place while the central disc 36 is rotatable in an oscillatory manner as shown in FIG. 3A, other configurations are possible. For example, in another embodiment, the central disc 36 can be fixed in place or stationary while the outer ring 32 is rotated in an oscillatory manner, as shown in FIG. 3B. In yet another embodiment, both the outer ring 32 and the central disc 36 are rotated in an opposing oscillatory manner, as shown in FIG. 3C, via one or more drive motors. In this embodiment, the motion of the outer ring is out of phase with the central disc. In that way, when the outer ring moves counterclockwise, the central disc moves clockwise, and vice versa.

In accordance with aspects of the present disclosure, the gripping surface 40 adjacent an inner edge 42 of outer ring 32 and gripping surface 46 adjacent an outer edge 48 of the central disc 36 can be provided with a friction enhancing texture, as shown in FIGS. 1-3C. The friction enhancing texture aims to reduce slippage between the respective surface and the subject's skin, thereby reducing abrasions. In the embodiment shown in FIG. 2, both of these surfaces are knurled. However, other friction enhancements can be employed, such as providing a surface roughness via machining or, for example, a grit dispersed coating or the like. Other techniques for preventing slippage between the surfaces 40 and 46 and the subject's skin are also possible, including, for example, the creation of a vacuum between the respective surfaces/skin. In some embodiments of the present disclosure, the gripping surfaces have a friction coefficient of greater than 0.5 against the skin.

One example of a method for treating a subject's skin with the apparatus 20 will now be described with reference to FIGS. 1-4. The subject's skin can be dry or wet, hydrated or dehydrated. First, the on/off button is activated, which allows the drive motor assembly 60 to move the central disc 36 in an oscillatory manner with respect to the outer ring 32. It will be appreciated that either the central disc 36, the outer ring 32, or both, can be oscillated by the drive motor assembly 60. Next, the shear inducing head 24 of the apparatus 20 is placed in contact with a selected area of the subject's skin.

Once contacting the subject's skin, the movement of the adjacent surfaces 40 and 46 creates highly localized shear forces suitable to open only the stratum corneum (SC) of the subject's skin. When the edges 42 and 48 slide past each other a pre-determined amount α, sufficient shear levels are produced to open or part the skin in a shear region. The shear levels are a function of the gap A, the amount of respective movement α, and the static friction between the surfaces 40 and 46 and the subject's skin. As a result, layers of the SC part or open, creating fissures therein within the intended shear region. Parting of the skin can refer to a rupture of the desmosome and lipid binding of the corneocytes of the SC.

The shear inducing head 24 can be traversed over one or more areas of the subject's skin. Once the desired areas of the subject's skin are treated, the apparatus 20 can be removed from the subject's skin, and the apparatus powered down. A skin formulation can then be applied to the treated areas of the subject's skin.

The skin formulation can be a "dermatological composition" or a "cosmetic composition." Among the compositions that can be applied to the skin by the dispensing device and used conjointly with the workpiece/appliance may be one or more of: slimming agents, humectants or moisturizers, anti-ageing substances, in particular "anti-wrinkle" substances, anti-oxidants, fat-restructuring substances, substances acting on the micro-circulation, biological active substances known for their actions on the mechanotransduction chain, tensioning agents which fix the immediate deformations conferred by the suction on the surface of the skin and thereby lead to a temporary smoothing of the skin, and any dermatological compositions including but not limited to a) econazole and its salts, like sodium, potassium, lithium, calcium, magnesium, nitrate or ammonium salts; b) flavones such as flavone, apigenine, chrysine, flavanone, quercetine; and c) retinoic acid.

Figure 5:
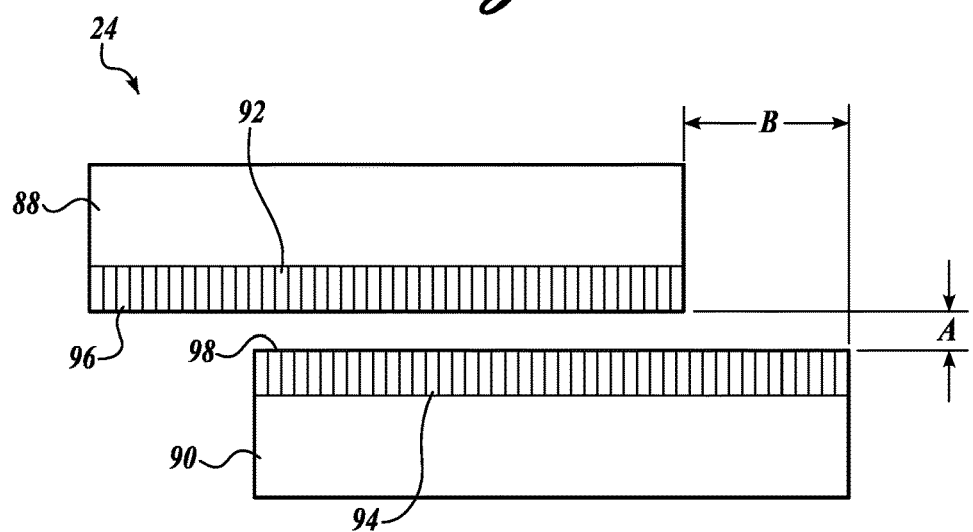
FIG. 5 is a schematic representation of another shear inducing head formed in accordance with aspects of the present disclosure.

To this point, the various embodiments have employed a shear inducing head 24 that employs a rotationally (i.e., angularly) oscillatory motion to one or both head components 32 and 36. It will be appreciated that in other embodiments of the present disclosure, the shear inducing head 24 may employ linearly oscillatory, sometimes referred to as reciprocating, motion to one or both head components, such as parallel disposed members 88 and 90, as shown schematically in FIG. 5. In this embodiment, parallely disposed members 88 and 90 include respective first and second gripping surfaces 92 and 94 adjacent first and second edges 96 and 98. The first and second gripping surfaces 92 and 94 in some embodiments have a width of between about one (1) and five (5) mm or greater. The edges 96 and 98 oppose one another and are separated by a constant gap of width A. The drive motor assembly 60 can be configured in some embodiments to oscillate the first gripping surface 92 with respect to the second gripping surface 94, back and forth a distance B of between about 0.003 mm and 0.200 mm or greater and with a frequency of between 10-400 Hz in some embodiments and between about 100-150 Hz in certain embodiments. It will be appreciated that either member 88 or member 90, or both, can be reciprocated by the drive motor assembly 60. Embodiments in the head 24 may also include a plurality of members alternatingly disposed and spaced apart via gaps A.

It should be noted that for purposes of this disclosure, the use of "including," "comprising," or "having" and variations thereof is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The invention claimed is:

1. A skin treatment apparatus, comprising:
a shear inducing head having a first friction surface adjacent a first edge, and a second friction surface adjacent a second edge, which is spaced a constant distance from the first edge in order to form a gap having a width of between about 0.003 mm and 0.200 mm; and
a drive motor assembly configured to impart an oscillating motion to the shear inducing head such that the first friction surface moves by one of angular motion with an amplitude of less than 3.4 degrees and linear motion with an amplitude of less than 0.200 mm with respect to the second friction surface in an oscillating manner, wherein the first friction surface is configured to grip a first skin portion with a static friction coefficient of greater than 0.5 and the second friction surface is configured to grip a second skin portion with a static friction coefficient of greater than 0.5 such that during the oscillating motion, the first and second friction surfaces do not slip with respect to the first and second skin portions, respectively, and the shear inducing head is able to induce shear in a Stratum Corneum layer of skin by movement between the respective friction surfaces without inducing trauma in skin layers below the Stratum Corneum layer of skin.

2. The skin treatment apparatus of claim 1, wherein the oscillating motion has a frequency of about 100-400 hz.

3. The skin treatment apparatus of claim 1, wherein the oscillating motion is angular and has an amplitude between about 0.1 degrees and 3.4 degrees.

4. The skin treatment apparatus of claim 1, wherein the oscillating motion is linear and has an amplitude of between about 0.003 mm and 0.200 mm.

5. The skin treatment apparatus of claim 1, wherein the first and second friction surfaces include a friction enhancement.

6. The skin treatment apparatus of claim 5, wherein the friction enhancement includes one of a knurl, a texture, and a surface treatment.

7. The skin treatment apparatus of claim 1, wherein the oscillating motion is angular, and wherein the first friction surface is disposed on an outer ring and the second friction surface is disposed on a central disc.

8. The skin treatment apparatus of claim 7, wherein the central disc has a diameter of between about one (1) mm and 20 mm.

9. The skin treatment apparatus of claim 7, wherein the drive motor assembly is coupled to the central disc.

10. The skin treatment apparatus of claim 9, wherein the drive motor assembly is coupled to the central disc and the outer ring in order to impart opposing oscillating motion thereto.

11. The skin treatment apparatus of claim 1, wherein the first and second surfaces are disposed on first and second parallely extending members.

12. A method for applying shear force to skin, the method comprising: providing a shear inducing head having a first member and a second member, the first and second members spaced at a constant distance between about 0.003 mm and 0.200 mm apart and defining first and second skin gripping surfaces, respectively, each of the first and second skin gripping surfaces having a static friction coefficient of greater than 0.5;
oscillating the first skin gripping surface by one of angular motion at an amplitude between about 0.1 degrees and 3.4 degrees and linear motion at an amplitude between about 0.003 mm and 0.200 mm, the first skin gripping surface oscillating at a selected frequency with respect to the second skin gripping surface; and
contacting the shear inducing head to a region of the skin to impart relative movement of a first skin portion and a second skin portion such that during the oscillation, the first and second skin gripping surfaces do not slip with respect to the first and second skin portions, respectively, and the shear inducing head is able to induce shear in a Stratum Corneum layer of the skin therebetween without inducing trauma in skin layers below the Stratum Corneum layer of skin.

13. The method of claim 12, wherein the selected frequency is about 100-400 hz.

14. A method for infusing a skin formulation into a user's epidermis, comprising:

providing a shear inducing head having a first member and a second member, the first and second members spaced at a constant distance between about 0.003 mm and 0.200 mm apart and defining first and second skin gripping surfaces, respectively, each of the first and second skin gripping surfaces having a static friction coefficient of greater than 0.5 such that the first skin gripping surface and the second skin gripping surface do not slip with respect to a first skin portion and a second skin portion, respectively;

oscillating the first skin gripping surface by one of angular motion at an amplitude less than about 3.4 degrees and linear motion at an amplitude less than about 0.200 mm:

contacting the shear inducing head to a region of the skin to impart relative movement of the first skin portion and the second skin portion such that the shear inducing head is able to induce shear in a Stratum Corneum layer of the skin therebetween without inducing trauma in skin layers below the Stratum Corneum layer of skin, thereby defining sheared areas of skin; and applying a skin formulation to the sheared areas of skin.

15. The method of claim 14, further comprising oscillating the first skin gripping surface at a selected frequency between about 100 hz and 400 hz with respect to the second skin gripping surface.

16. The method of claim 14, wherein oscillating the first skin gripping surface is by angular motion and has an amplitude between about 0.1 degrees and 3.4 degrees.

17. The method of claim 14, wherein oscillating the first skin gripping surface is by linear motion and has an amplitude between about 0.003 mm and 0.200 mm.

* * * * *